(12) United States Patent
Trainoff (10) Patent No.: US 7,982,875 B2
(45) Date of Patent: Jul. 19, 2011

(54) METHOD AND APPARATUS FOR MEASURING THE SCATTERED LIGHT SIGNALS FROM A LIQUID SAMPLE

(75) Inventor: Steven P. Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 170 days.

(21) Appl. No.: 12/456,470

(22) Filed: Jun. 15, 2009

(65) Prior Publication Data

US 2010/0315637 A1 Dec. 16, 2010

(51) Int. Cl.
*G01N 21/00* (2006.01)
(52) U.S. Cl. .................................. 356/337; 356/343
(58) Field of Classification Search ........... 356/335–344
See application file for complete search history.

(56) References Cited

U.S. PATENT DOCUMENTS

| | | | |
|---|---|---|---|
| 4,541,719 A * | 9/1985 | Wyatt | 356/343 |
| 4,565,448 A * | 1/1986 | Abbott et al. | 356/336 |
| 4,591,268 A * | 5/1986 | Lew | 356/338 |
| 4,616,927 A | 10/1986 | Phillips et al. | |
| 4,673,289 A * | 6/1987 | Gaucher | 356/72 |
| 4,907,884 A | 3/1990 | Wyatt et al. | |
| 4,952,055 A | 8/1990 | Wyatt | |
| D329,821 S | 9/1992 | Wyatt et al. | |
| 5,175,596 A * | 12/1992 | Dick et al. | 356/442 |
| 5,305,071 A | 4/1994 | Wyatt | |
| 5,404,217 A * | 4/1995 | Janik et al. | 356/246 |
| 5,495,333 A * | 2/1996 | Konda et al. | 356/339 |
| 5,530,540 A | 6/1996 | Wyatt et al. | |
| 6,052,184 A * | 4/2000 | Reed | 356/338 |
| 6,426,794 B1 | 7/2002 | Trainoff | |
| 6,452,672 B1 | 9/2002 | Trainoff | |
| 7,057,724 B1 * | 6/2006 | Mead et al. | 356/343 |
| 7,151,604 B2 * | 12/2006 | Saccomanno et al. | 356/343 |
| 7,215,475 B2 * | 5/2007 | Woodgate et al. | 359/624 |

OTHER PUBLICATIONS

Wyatt Technology Corporation, Dawn Heleos II promotional literature, 2007, Wyatt Technology Corporation, Goleta, USA.
Wyatt Technology Corporation, Dawn Treos promotional literature, 2006, Wyatt Technology Corporation, Goleta, USA.

* cited by examiner

*Primary Examiner* — Gregory J Toatley
*Assistant Examiner* — Jarreas C. Underwood
(74) *Attorney, Agent, or Firm* — Philip J. Wyatt; David N. Villalpando (57) ABSTRACT

A sample cell for making light scattering measurements, incorporating an exterior surface acting as both a lateral and vertical lens, is described. This unique structure permits greatly improved measurement of the light scattered by molecules and particles suspended in a fluid contained therein or flowing therethrough while illuminated by a fine light beam incident thereon. The resultant lensed structure of the cell, when integrated into a scattered light photometer and combined with suitable apertures before each scattered light collecting detector, reduces significantly stray light from entering each such detector.

29 Claims, 8 Drawing Sheets

Prior Art

FIGURE 1

PRIOR ART

PRIOR ART

METHOD AND APPARATUS FOR MEASURING THE SCATTERED LIGHT SIGNALS FROM A LIQUID SAMPLE

RELATED PATENTS AND APPLICATIONS

The following patents and application concern methods and apparatus related to applications of the present invention.

G. R. Janik and P. J. Wyatt, U.S. Pat. No. 5,404,217 (4 Apr. 1995) "Laser liquid flow cell manifold system and method for assembly."

P. J. Wyatt and G. R. Janik, U.S. Pat. No. 5,530,540 (25 Jun. 1996) "Light scattering measurement cell for very small volumes."

S. P. Trainoff, U.S. Pat. No. 6,426,794 (30 Jul. 2002) "An optical flow cell incorporating automatic self cleaning."

S. P. Trainoff, U.S. Pat. No. 6,452,672 (17 Sep. 2002) "A self cleaning optical flow cell."

S. Trainoff and P. J. Wyatt, U.S. Pat. No. 6,651,009 (18 Nov. 2003) "Method for determining average solution properties of macromolecules by the injection method."

P. J. Wyatt and M. J. Weida, U.S. Pat. No. 6,774,994 (10 Aug. 2004) "Method and apparatus for determining absolute number densities of particles in suspension."

S. P. Trainoff, U.S. Pat. No. 7,386,427 (10 Jun. 2008) "Method for correcting the effects of interdetector band broadening."

D. I. Some and S. P. Trainoff, U.S. patent application Ser. No. 12/072,986, filed 29 Feb. 2008, "Method for determining average properties of molecules in solution by injection into a flowing solvent."

S. P. Trainoff, U.S. patent application Ser. No. 12/148,358, filed 18 Apr. 2008, "Method to derive physical properties of a sample after correcting the effects of interdetector band broadening."

BACKGROUND

Solutions containing solutes such as molecules, viruses, nanoparticles, liposomes, etc. are often measured following separation by chromatographic techniques or other types of preparative techniques. Such measurements may include determination of solute concentration, solution viscosity, and light scattering properties. The latter measurement used in combination with a corresponding concentration determination may be used to derive the size, molar mass, aggregation, and associations of the solutions constituent elements. To improve such determinations, the light scattering measurement is often performed by measuring the scattered light at a plurality of angles with respect to the direction of an associated light beam such as produced by a laser. Such measurements are referred to as multiangle light scattering or MALS for short and are performed by absolute light scattering photometers or their derivatives.

A dramatic improvement in the ease by which such MALS measurements might be performed occurred with the introduction of an axial flow cell described initially in U.S. Pat. No. 4,616,927, referred to hereinafter as the '927 patent. Further refinements, especially as to the means by which the cell was integrated into the photometer, are described in corresponding U.S. Pat. Nos. 5,530,540, 4,952,055, 4,907,884 and design Pat. Des 329,821.

The basic structure of the so-called axial flow cell consists of a right cylinder with a small polished bore through a diameter about midway between the cylinder's base and top. Both the sample and the incident light beam thereon pass through this same bore. This is quite different from more conventional illumination systems wherein the illuminating beam is usually transverse to the solution flow direction. For the axial cell flow, the cell itself acts as a cylindrical lens imaging paraxial rays from light scattered from different parts of the beam onto a set of detectors surrounding it and lying on a plane through the bore and parallel to the cell base. Also of great importance is the enablement of measurements at smaller scattering angles when the cell refractive index is greater than the fluid refractive index, which is usually the case. Although the performance of light scattering photometers that incorporate the '927 axial flow cell is far better than most other flow cell embodiments, there remain some important elements associated with the collection of the scattered light that will benefit from an improved structure. The primary objective of this invention is to address these elements and provide methods and means to enhance the overall performance of the photometer in which the sample cell plays a greater role in collecting the light scattered by the solution flowing through it.

As mentioned, the lens-like behavior of the flow cell structure permits the focusing of paraxial rays from the central illuminating beam onto an arc containing the scattered light detectors. However, only rays very close to those leaving the cell in the plane parallel to the cell base can reach the detectors. Most of the light scattered toward the detectors is refracted out of the detector plane and not collected. In addition, some stray light from the liquid/glass-bore interfaces will reach the detectors increasing, thereby, the background contributions to the signals being collected. The success of the '927 cell design in expanding significantly the fields of molecular biology, analytical chemistry, nanoparticle characterization and others by their adoption and use of light scattering techniques have provided significant impetus to develop new cell structures and applications.

It is a major objective of this invention to increase the efficiency of collecting light scattered from the light beam illuminated solutions. Another objective of this invention is to improve the signal-to-noise ratio of the collected scattering signals by means of a light collecting structure whereby spatial filtering may reduce stray light contributions significantly.

SUMMARY OF THE INVENTION

By means of a redesigned axial flow cell, the measurement of light scattered by solutes flowing therethrough may be improved. In its preferred embodiment, this cell is designed to capture a greater fraction of the light so scattered while providing means to permit reduction of stray light entering each of the circumscribed plurality of detectors. The flow cell, thus achieved, incorporates a surface of rotation that focuses light scattered by the entrained solution far more efficiently than the cylindrical structure of the '947 invention. By focusing the scattered light on the detectors, the inventive structure may now be combined with spatial filtering to reduce significantly stray light originating from the walls of the flow-confining cell bore.

DETAILED DESCRIPTION OF THE INVENTION

Figure 1:
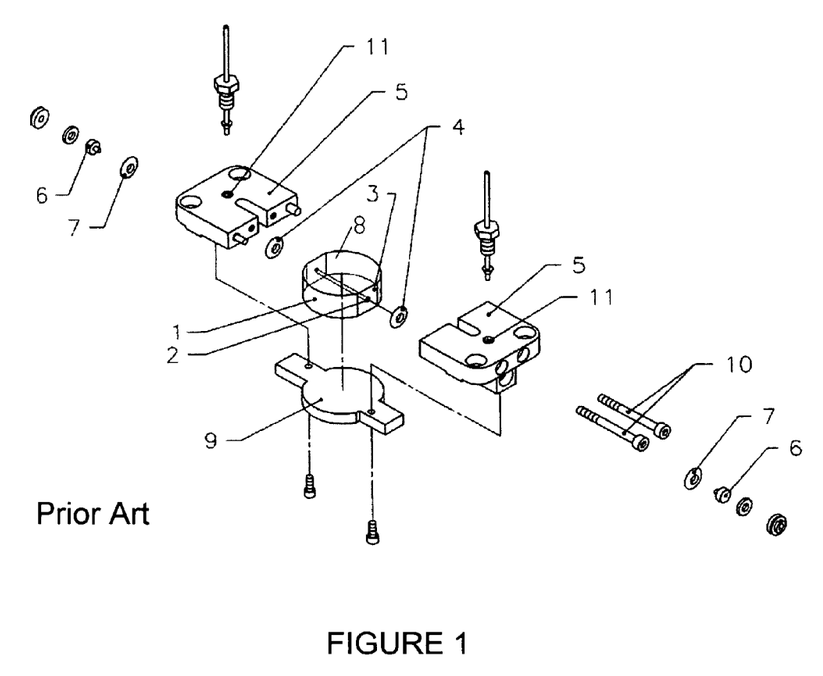
FIG. 1 shows a flow cell of the prior art with some of fittings for insertion into a light scattering photometer.

FIG. 1 shows the axial flow cell of the prior art '947 invention together with the typical set of fittings required to maintain its position within a photometer and permit its use for measuring light scattered from a sample flowing through the cell. The cell 1 is made of a transparent medium such as glass or plastic, in the form of a right cylinder of radius R, is flattened on two sides 3 to permit seals 4 to be held thereagainst. Throughout this specification, the cell's composition will be referred to as being of glass, although it may be made of any other transparent medium suitable for the solutions that would pass therethrough. Through its center and along a diameter is a polished bore 2 whose cross section may be circular or rectangular, generally in the range of 0.5 to 1.5 mm. Two manifolds 5 hold the cell against said seals. Windows 6 held by fittings against seals 7 permit a fine beam of light to pass therethrough. The light is generally from a laser source and polarized perpendicular to the cell base of the right cylinder structure. The manifolds are held together by means of a base plate 9 and bolts 10. A fluid sample may be introduced and removed through fittings 11.

Figure 2:
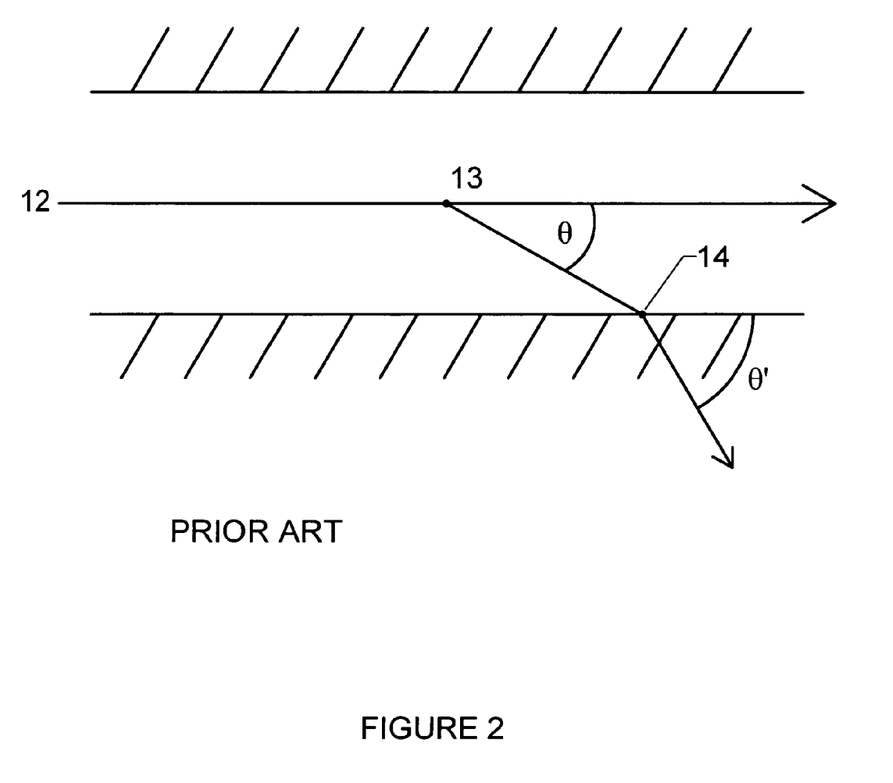
FIG. 2 shows the refraction of scattered light originating at the center of the bore of the prior art cell; a feature common with the present invention.

FIG. 2 shows details of the refractions within the bore of the prior art retained in the present invention. Shown therein is the geometry of incident light beam 12 scattered by the sample at the center of the cell 13 into the direction $\theta$ and refracting at the air-glass interface 14 into the direction $\theta'$. The liquid solution passing therethrough is of refractive index $n_s$ and the glass is of refractive index $n_g$ with generally $n_s < n_g$. Thus, the light scattered at angle $\theta$ within the liquid has been transformed into a refracted ray that will leave the bore at an angle $\theta'$. This was an important element of the prior art cell since the scattering at small scattering angles is transformed by refraction at the solution glass interface to larger scattering angles that are more experimentally accessible. In the discussion that follows, it is to be understood that $\theta_g$ will refer to the angle of the scattered light in the glass, after the Snell's law correction has been performed ($\theta'$ in the '947 patent). The final refractions at the cell's air-glass interfaces will be key items of importance.

Figure 3:
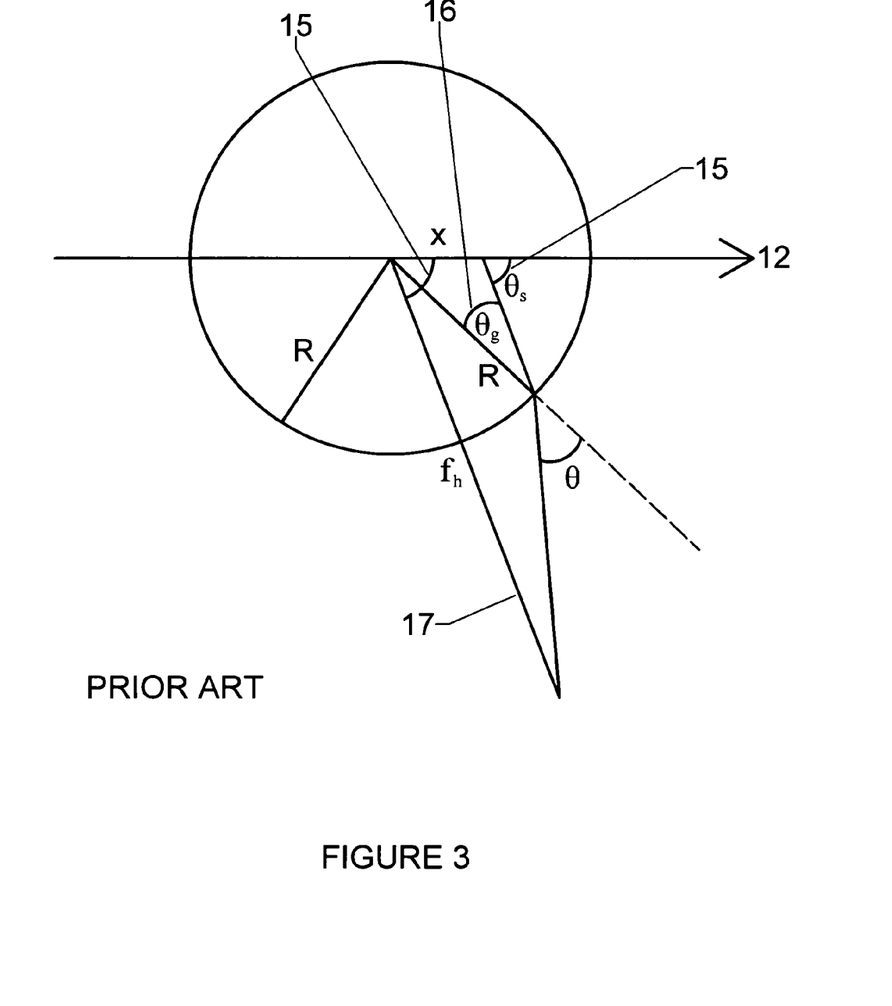
FIG. 3 shows a top view of the scattering geometry of the prior art within the plane containing the bore and parallel to the cell base.

Another advantage of this cell geometry is that the cylindrical lens formed by the exterior of the cell focuses light along the beam that scatters at any scattering angle $\theta_s$, indicated by the arcs 15 of FIG. 3, with respect to the direction of the incident light beam 12 to a ring on which detectors may be placed at a distance $f_h$ from the center of the cell. Further details of the cell geometry of this prior art is shown in FIG. 3. The beam acts as a line source along the horizontal axis. Let the radius of the cell be R, and let its index of refraction be n. Consider the ray that is emitted from the center of the cell at an angle $\theta_s$ from the main beam, and another that is emitted at the same angle at a distance x further along the beam. From Snell's law a ray from the center of the cell incident 16 at an angle $\theta_g$ with respect to the line 17 obeys $$n \sin \theta_g = \sin \theta. \tag{1}$$

From the law of sines one has $$\frac{\sin(\pi - \theta)}{f_h} = \frac{\sin(\theta - \theta_g)}{R}. \tag{2}$$

If only paraxial rays are considered, $\theta=1$ and $\theta_g=1$, one gets $$f_h = R \frac{n}{n-1}. \tag{3}$$

Note, it is not necessary to assume that $\theta_s$ is small; the same result is obtained for paraxial rays at all scattering angles.

Figure 4:
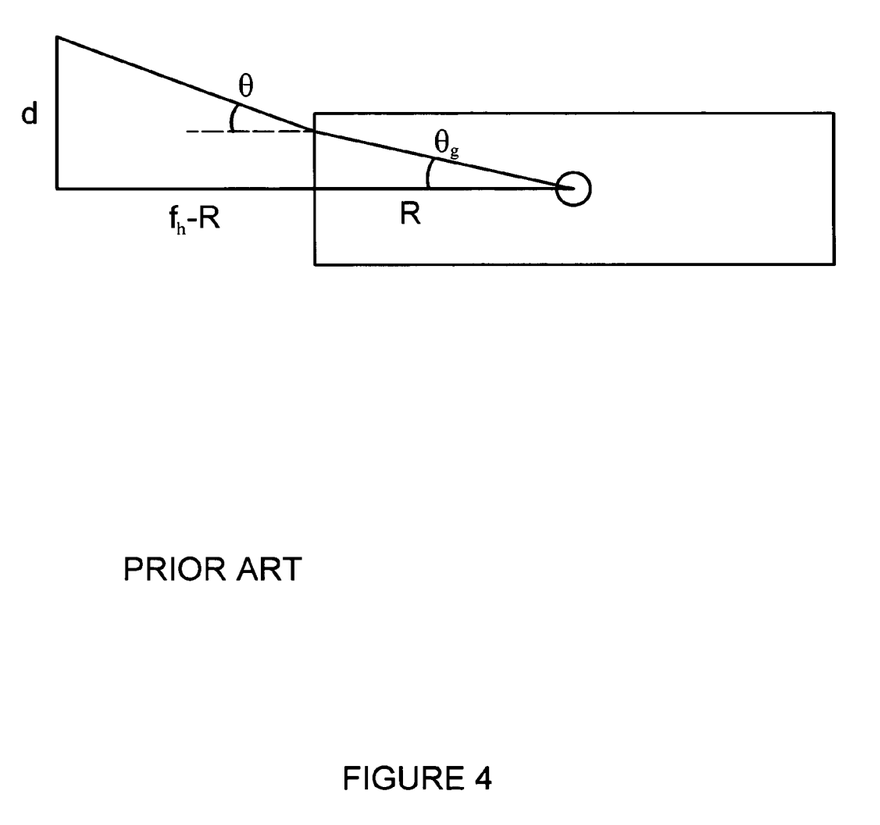
FIG. 4 shows a side view of the prior art cylindrical cell geometry.

Consider now the light collected by the detectors based on the cylindrical cell of the prior art placed at the distance $f_h$ from the center of the cell. This geometry is shown in FIG. 4. If the detector is of radius $\rho$ and is located at the focal ring, the range of collection angles may be calculated. Again, for the paraxial case, one has $$\theta_g \approx \left( \frac{\rho}{n f_h - (n-1)R} \right). \tag{4}$$

For focal length, $f_h$, given by Eq. (3), Eq. (4) becomes $$\theta_g \approx \left( \frac{\rho}{R} \frac{n-1}{2n-1} \right). \tag{5}$$

For a detector or radius 1.5 mm and a cell of radius 16 mm and n=1.5, $\theta_g \approx 23$ mrad. The actual collection area is somewhat smaller since the detectors are usually circular, not square, however it is important to note that this is a small fraction of the total scattered light originating from the sample.

Consider now a key element of the present invention: means to provide more efficient capture of the light scattered by a sample within a flow cell by using a novel cylindrical lens to collect more light in the azimuthal direction (out of the scattering plane), while minimizing averaging in the axial direction (in the scattering plane). This is important because all multi-angle light scattering instruments measure the scattering intensity as a function of the axial angle ($\theta$) and averaging in this direction distorts the data and makes fitting to a model problematic. Averaging in the azimuthal direction is free from this problem. The means by which the collection efficiency is increased is by modification of the prior art cell surface in its vertical direction to integrate the convex lens structure shown in FIG. 5. Although the theory has been developed for such integration of a convex lens structure to provide focusing in the vertical direction, it will be understood by those skilled in the art that such vertical focusing may be achieved also by means of the circumferential integration of Fresnel lens elements. Alternatively, the continuous convex structure providing vertical focusing may be replaced by discrete cylindrical lens elements positioned in proximity to the flat circular surface and each providing vertical focusing on to its associated detector.

Figure 5:
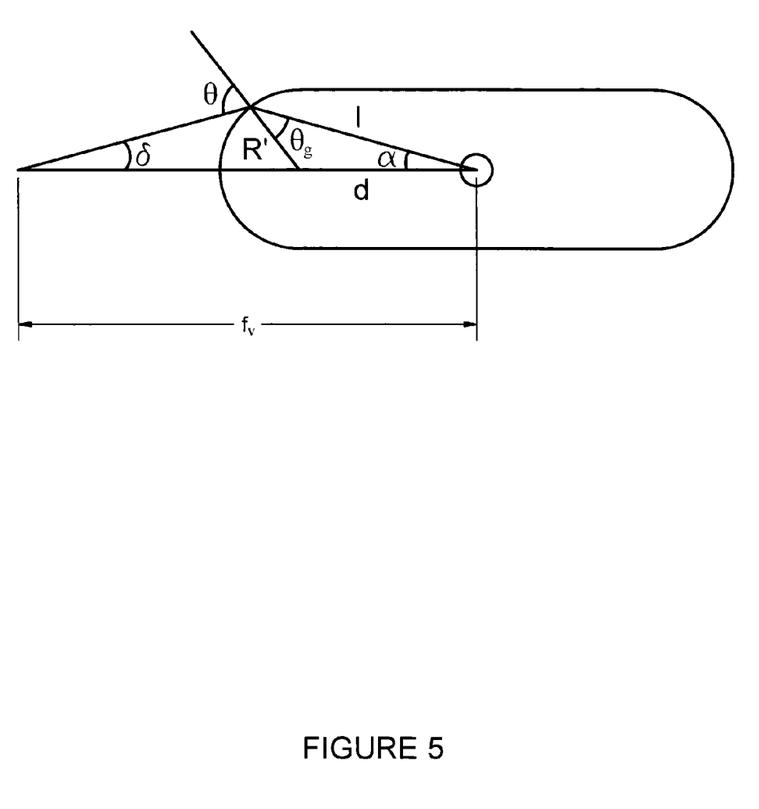
FIG. 5 shows a side view of the new cell shape.

The distance between the center of the cell and center of the inventive convex region of radius R' is d. A scattered ray leaves the illuminated sample at an angle $\alpha$ and intersects the circular surface at a distance l from the center of the bore making an angle $\theta_g$ with respect to the normal thereto. Applying the law of cosines and law of sines yields $$l^2 = R'^2 + d^2 + 2R'd\cos(\pi - \alpha - \theta_g) \quad (6)$$

$$\frac{\sin\theta_g}{d} = \frac{\sin\alpha}{R'} \quad (7)$$

It may be shown that the focal length is given by $$f_v = l\cos\alpha + l\frac{\sin\alpha}{\tan(\theta - \theta_g - \alpha)}. \quad (8)$$

This expression can be solved for a full aspherical lens design $f_v(\alpha)$, but it is much easier to solve in the paraxial approximation for which $$\theta \approx n\theta_g, \alpha \approx \theta_g R'/d, \text{ and } l \approx R'+d, \quad (9)$$

which yields a result independent of $\alpha$, viz.

$$f_v = d + \frac{ndR'}{(n-1)d - R'}. \quad (10)$$

In order to have the scattered rays focus at the same distance in both the horizontal and vertical directions, the two focal lengths are set equal $f_h = f_v$. Solving for the radius and recalling that $R = d + R'$ yields and $$R' = R\frac{n-1}{2n-1} \quad (11)$$

and $$d = R\frac{n}{2n-1} \quad (12)$$

This is a primary result. It relates the lens radius R' to the size of the cell R and the index of refraction of the glass n.

An important benefit of this inventive structure, relative to the structure of the prior art, is that it collects much more light. A simple numerical example will demonstrate this. Consider a glass cell of an index of refraction n=1.5 with an overall radius, R=16 mm, which is approximately the same size as the prior art cell. Let $f = f_h = f_v = 3.0R$, R'=0.25R, and d=0.75R. The maximum collection angle of the structure of FIG. 5 is simply $$\alpha = \tan^{-1}\left(\frac{R'}{d}\right) \quad (13)$$

which gives $\alpha$=322 mrad. This gives rise to a collection efficiency increase by an order of magnitude. This analysis is only approximate since it ignores the actual shape the detector as well as the efficiency for collecting non-paraxial rays. However, it demonstrates that there will be a significant increase in the detector signal levels. For instrumentation in which the detectors are in the shot noise limit, the detector noise will increase as the square root of the signal giving rise to an expected S/N improvement of over a factor of 3.

Figure 6:
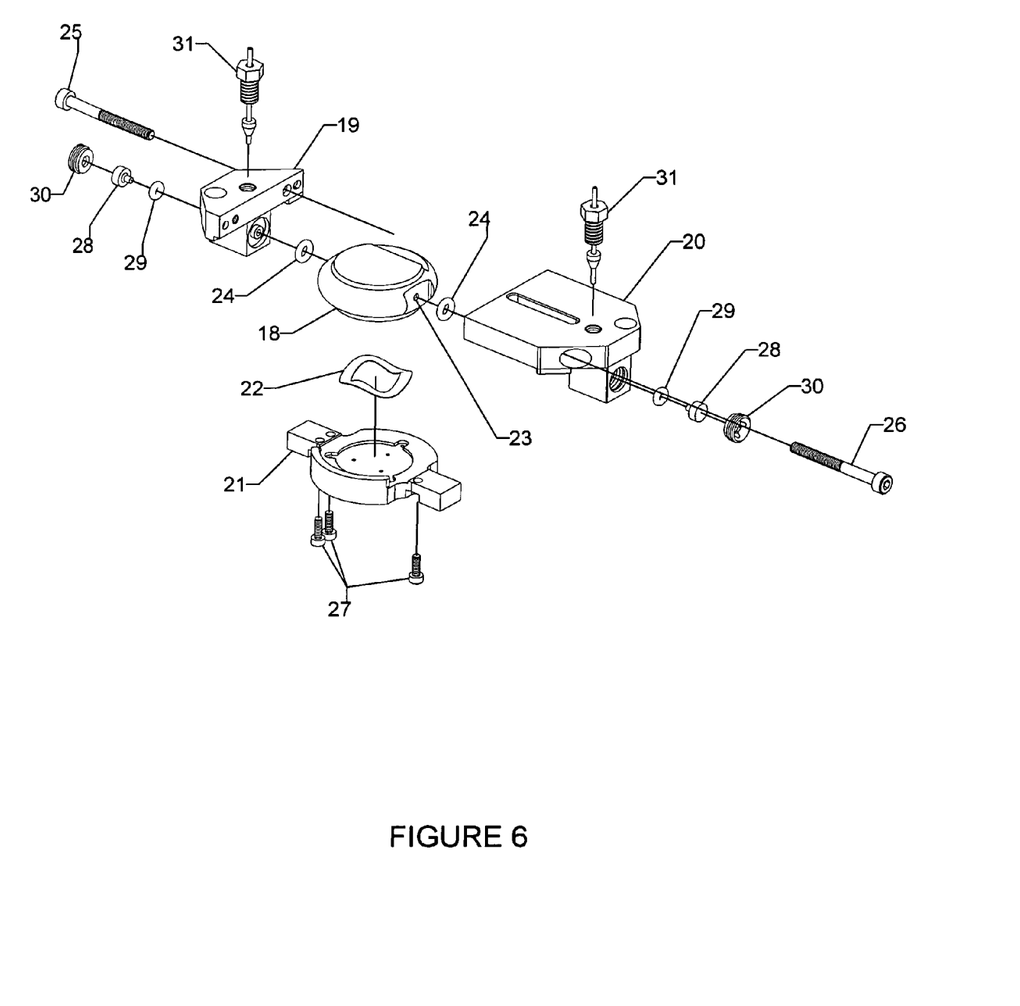
FIG. 6 shows the new flow cell of the present invention with some fittings.

FIG. 6 shows a rendering of the inventive cell 18 and the major fittings required to maintain its position and function within a light scattering photometer. The cell is held by manifold means 19 and 20 and bottom plate 21. A spring washer 22 insures contact of the cell with said manifolds. The axial bore 23 through the cell is connected with the manifolds so that liquids may flow unimpeded therethrough by O-rings seals 24. Threaded bolts 25, 26, and 27 hold said cell manifolds and bottom plate 21 in a single assembly. A fine light beam may pass through said assembly by means of windows 28 sandwiched between O-ring seals 29 and threaded fittings 30. Fluid solutions may flow through said sealed assembly containing connective passages through said manifolds into said bore by means of threaded fittings 31 permitting connection to chromatographic apparatus, pumps, sampling sources, etc. It should also be noted that the optical windows could be incorporated into the cell structure itself by means, for example, of the fluid entrance and exit ports being machined directly into the cell and flattening the ends so as to permit the beam to enter and exit normal to the axial bore.

The analysis above that led to the results of Eqs. (11) and (12) represents but a simple example of the inventive method and the apparatus developed to achieve significantly improved scattered light collection efficiency. The convex structure of the corresponding cell has been selected of a simple circular form for which the paraxial approximation may be used. It also has the benefit of being fabricated easily. However, it is also possible to solve Eq. (8) analytically or numerically to create an aspheric surface of revolution that further increases the collection efficiency. Thus the invention teaches of a general method of improving the performance of a light scattering cell.

Figure 7:
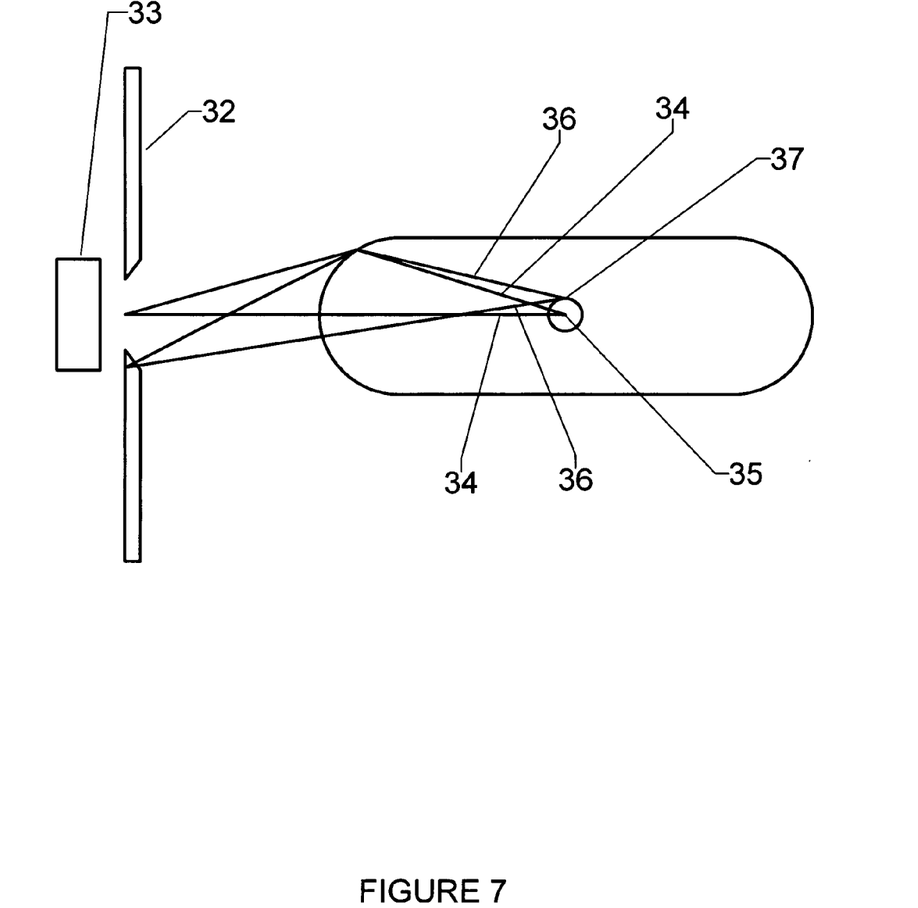
FIG. 7 shows a side view of the suitably selected slit structure that rejects secondary scattered light from bore surfaces.

A further advantage of the inventive method and apparatus relates to the ability of the new embodiments to simplify the elimination of significant amounts of stray light. Since the inventive flow cell described images the beam inside the flow cell to detectors lying on a ring at distance f therefrom, this results in a geometry particularly amenable to spatial filtering. In order to reject secondary scattered light from the edges of the flow cell bore, one need only put a slit 32 in front of each such detector 33 lying on said focal ring as shown in FIG. 7. Shown thereon are two sets of scattered rays: those originate at the sample 34 that is illuminated at the center of the bore 35 and those that originate from stray light 36 at the bore-liquid interfaces 37.

One goal of the inventive design is to maximize the collection of scattered light from the cell. By means of the inventive cell, a small range of azimuthally scattered light is captured at each polar angle by the detector placed to receive it on the scattering ring previously described. The variation of scattered light intensity into a given polar direction as a function of azimuthal angle $\phi$, for the case of vertically polarized incident light, is proportional to $\cos^2 \phi$ for particles whose size is very small relative to the wavelength of the incident light beam. For larger particles, one may detect changes in the polar scattering with changes of azimuthal angle. Such changes may also be seen for particles that depolarize the incident light. Accordingly, it may be desirable to measure the scattered light in planes not perpendicular to the incident radiation. This could be achieved easily by rotating the plane of polarization of the incident light by means, say, of a variable half wave plate. Nevertheless, such measurements, in order to record the azimuthal scattering properties of the illuminated particles, would require a separate measurement for each orientation of the plane of polarization. Since the sample already scatters the radiation into all azimuthal directions, it would seem desirable to collect such scattered light from different azimuthal scattering planes at the same time. This may be achieved by an extended structure as shown on FIG. 8. This multiple lensed structure permits thereby measurements incorporating the improvements of a single lensed cell at different orientations with respect to the plane of polarization of the incident light beam. As has been discussed previously, the inventive design operates by imaging the line source of scattered light onto a ring lying on a common scattering plane in space by means of the novel cylindrical lens. Different lens elements associated with measurements of light scattered into different scattering planes with respect to a common bore 38 are shown at 39, 40, and 41. A generalized structure forming a series of lenses covering the entire range of azimuthal angles is shown to the right at 42. Note, however, that the range of azimuthal angles focused to the corresponding scattering ring must be the same for each polar direction. Thus the range of the collection angle α is reduced as the polar angles approach 0° and 180°. Indeed, $\alpha \propto \sin \theta$.

Figure 8:
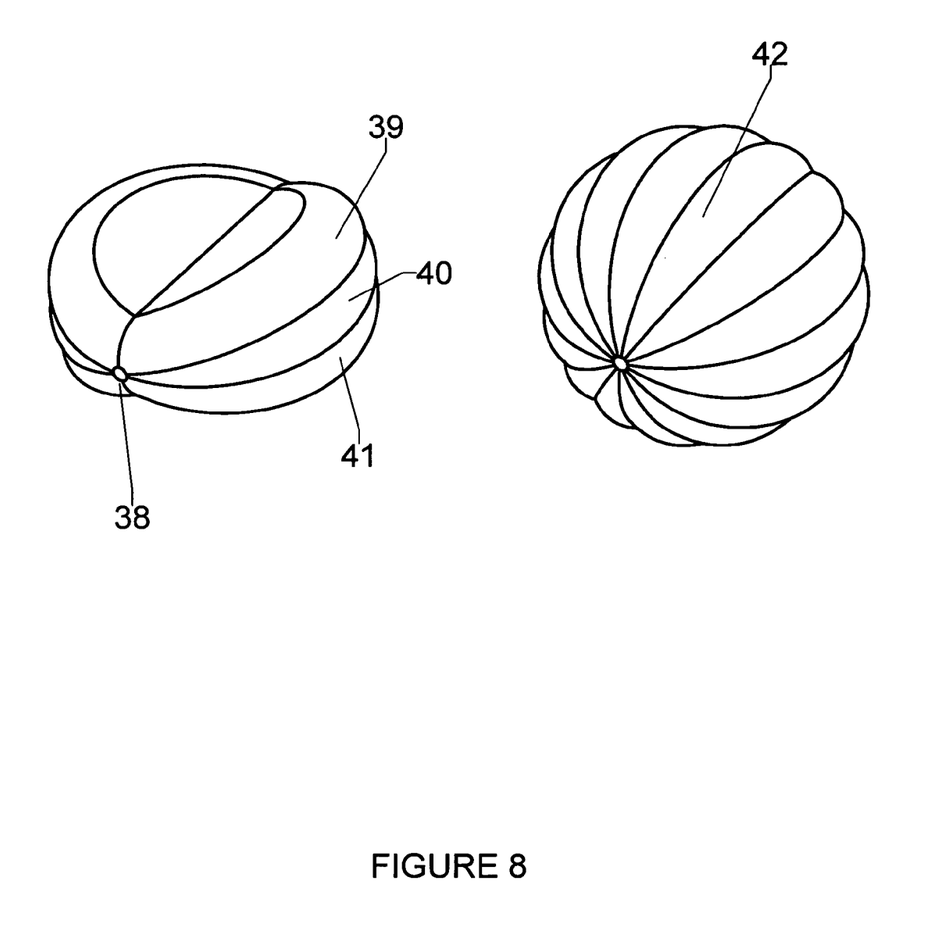
FIG. 8 shows an embodiment of the invention incorporating multiple lensed structures.

Under favorable circumstances, if the samples are of high enough concentrations and moving slowly enough through the flow cell, then it may be possible to alternate between changing the plane of polarization and collecting a complete set of scattered data rapidly enough to capture the same amount of information as possible with the integrated structure of FIG. 8.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A circular sample cell for measuring the light scattering properties of a liquid suspension of particles, whose body portion,
   1) includes an interior bore disposed along a diameter, to hold a liquid suspension of particles and along which a fine beam of light may pass illuminating said liquid suspension to scatter light from said particles;
   2) has means at both openings of said bore permitting the incorporation of said cell into manifold means to hold and position it with fittings to allow the flow of said liquid suspensions therethrough;
   3) has an exterior surface configured to act as both a lateral lens and vertical lens to focus light scattered from said illuminated bore into a common scattering angle to a single corresponding common focal point on a concentric detection ring.

2. The sample cell of claim 1, wherein said exterior surface is a surface of revolution about an axis normal to the horizontal plane containing the bore.

3. The sample cell of claim 2, wherein said exterior surface is of convex shape.

4. The sample cell of claim 3, wherein said convex shape has a constant radius of curvature about a point lying at a fixed distance from the center of said cell.

5. The sample cell of claim 4, wherein R is a radius of the sample cell in the horizontal plane containing the bore, R' is the fixed radius of curvature of the exterior surface whose center is at a distance d from the center of said sample cell, and n is the refractive index of the transparent material forming the sample cell, R being related to R' by the relationship:

$$R' = R\frac{n-1}{2n-1} \text{ and } d = R\frac{n}{2n-1}.$$

6. A system for measuring the light scattering properties of a liquid suspension of particles, comprising:
   1) a detection ring having a plurality of optical detectors, each detecting scattered light at each of a corresponding plurality of scattering angles;
   2) a sample cell
      a. having a circular body portion including an interior bore lying along a diameter thereof and in the same plane of said detection ring;
      b. having flattened, or otherwise modified, ends at both openings of said bore permitting the incorporation of said cell into manifold means to hold and position it with fixtures to permit the flow of said liquid suspension of particles through said bore;
      c. including an exterior surface that is a surface of revolution shaped to act as both a lateral lens and vertical lens to focus scattered light having a common scattering angle to a common focal distance on the detection ring;
   3) a manifold assembly
      a. Holding said cell in alignment within a light scattering photometer;
      b. Containing means and fittings to permit the introduction and flow of said liquid suspension through said bore; and
      c. Providing optical means as needed to permit the passage of a light beam along said bore such that said light beam illuminates and scatters from said liquid suspension of particles flowing therethrough.

7. The system of claim 6 wherein said sample cell's exterior surface of revolution integrates therein a Fresnel lens providing thereby vertical focusing of scattered light exiting therethrough.

8. The system of claim 6 wherein said vertical focusing is achieved by means of distinct cylindrical lensed elements placed in proximity to the flat circular surface providing lateral focusing of scattered light exiting therethrough.

9. The system of claim 6 wherein said optical means needed to permit the passage of a light beam through said bore are windows appropriately held in said manifold.

10. The system of claim 6 wherein said optical means needed to permit the passage of a light beam through said bore are incorporated into said cell structure.

11. The system of claim 6 wherein said optical detectors are each fitted with a corresponding slit that forms a spatial filter to reject secondary scattered light generated from the edges of said bore in said sample cell and into said corresponding scattering angle.

12. The system of claim 6 wherein said sample cell's exterior surface of revolution is of convex shape.

13. The system of claim 12 wherein said convex exterior surface has a constant radius of curvature about a point lying at a fixed distance from the center of said sample cell.

14. The system of claim 13, wherein R is a radius of said sample cell in the horizontal plane containing said bore, R' is the fixed radius of curvature of the exterior surface whose center is at a distance d from the center of said sample cell, and n is the refractive index of the transparent material forming the sample cell, R, R' and d are related as $$R' = R\frac{n-1}{2n-1} \text{ and } d = R\frac{n}{2n-1}.$$

15. The system of claim 11, wherein said secondary scattered light is stray light.

16. The system of claim 11, wherein said light beam is from a laser.

17. The system of claim 16, wherein said light beam from said laser is plane polarized perpendicular to the plane containing said detector ring.

18. The system of claim 16, wherein said light beam from said laser is plane polarized and the plane of polarization is at an angle other than 90 degrees to the plane containing said detector ring.

19. The system of claim 16, wherein said light beam from said laser is plane polarized and the angle of said plane of polarization may be changed by means of a variable half wave plate.

20. A method of measuring the light scattered by a liquid suspension of particles into each of a plurality of detectors placed on a ring surrounding a sample cell, comprising the steps of
1) selecting a sample cell
   a. having a circular body portion including an interior bore lying along a diameter thereof and in the same plane as said ring containing said detectors;
   b. having has means at both openings of said bore permitting the incorporation of said cell into manifold means to hold and position it with fittings to allow the flow of said liquid therethrough;
   c. having an exterior surface that is a surface of revolution formed to act as both a lateral and vertical lens that focuses all contributions of said scattered light having a common scattering angle to a common focal distance on said detector containing ring;
   d. positioned within said manifold means that
      i. holds said cell in alignment within a light scattering photometer;
      ii. contains means and fittings to permit the introduction and flow of said liquid suspension through said bore; and
      iii. provides optical means as needed to permit the passage of a light beam through said bore such that said light beam illuminates and scatters from said liquid suspension of particles flowing therethrough.
2) filling said interior bore with said liquid sample whose scattered light properties are to be measured;
3) passing a light beam along said bore; and
4) measuring the scattered light collected at each of said detectors placed on said surrounding ring.

21. The method of claim 20, wherein the surface of revolution is convex.

22. The method of claim 20, wherein a spatial filter is placed in front of each of said detectors to remove secondary light scattered by elements of said bore structure.

23. The method of claim 20, where said secondary scattered light is stray light.

24. The method of claim 20, where said light beam is from a laser.

25. The method of claim 24, where said light beam from said laser is plane polarized perpendicular to the plane containing said detector ring.

26. The method of claim 24, where said light beam from said laser is plane polarized and the plane polarization is at an angle not perpendicular to the plane containing said detector ring.

27. The method of claim 24, wherein said light beam from said laser is plane polarized and said angle of said plane of polarization may be changed by means of a variable half wave plate.

28. The method of claim 20 wherein said optical means needed to permit the passage of a light beam through said bore are windows appropriately held in said manifold.

29. The method of claim 20 wherein said optical means needed to permit the passage of a light beam through said bore are incorporated into said cell structure.

* * * * *